United States Patent
Kasemi et al.

(10) Patent No.: US 10,287,388 B2
(45) Date of Patent: May 14, 2019

(54) AMINE FOR LOW-EMISSION EPOXY RESIN COMPOSITIONS

(71) Applicant: SIKA TECHNOLOGY AG, Baar (CH)

(72) Inventors: Edis Kasemi, Zürich (CH); Andreas Kramer, Zürich (CH); Ursula Stadelmann, Zürich (CH); Urs Burckhardt, Zürich (CH)

(73) Assignee: SIKA TECHNOLOGY AGH, Baar (CH)

( * ) Notice: Subject to any disclaimer, the term of this patent is extended or adjusted under 35 U.S.C. 154(b) by 52 days.

(21) Appl. No.: 15/501,955

(22) PCT Filed: Aug. 7, 2015

(86) PCT No.: PCT/EP2015/068300
§ 371 (c)(1),
(2) Date: Feb. 6, 2017

(87) PCT Pub. No.: WO2016/023837
PCT Pub. Date: Feb. 18, 2016

(65) Prior Publication Data
US 2017/0226278 A1    Aug. 10, 2017

(30) Foreign Application Priority Data

Aug. 13, 2014  (EP) .................................... 14180870

(51) Int. Cl.
| | | |
|---|---|---|
| C08G 59/50 | (2006.01) | |
| C07C 211/18 | (2006.01) | |
| C07C 209/22 | (2006.01) | |
| C08G 59/22 | (2006.01) | |
| C07C 211/27 | (2006.01) | |

(52) U.S. Cl.
CPC ........ *C08G 59/5033* (2013.01); *C07C 209/22* (2013.01); *C07C 211/18* (2013.01); *C07C 211/27* (2013.01); *C08G 59/223* (2013.01); *C08G 59/5026* (2013.01); *C07C 2602/14* (2017.05)

(58) Field of Classification Search
CPC ............ C08G 59/5033; C08G 59/5026; C08G 59/223; C07C 211/18; C07C 211/27; C07C 209/22; C07C 2602/14
USPC .......................................................... 528/88
See application file for complete search history.

(56) References Cited

U.S. PATENT DOCUMENTS

| | | | | |
|---|---|---|---|---|
| 4,959,135 A | * | 9/1990 | Zenner ................ | C01B 13/0244 204/233 |
| 2013/0261270 A1 | * | 10/2013 | Butikofer .............. | C07C 211/09 525/423 |

FOREIGN PATENT DOCUMENTS

EP        2 465 843 A1    6/2012

OTHER PUBLICATIONS

Sep. 18, 2015 International Search Report issued in International Patent Application No. PCT/EP2015/068300.

* cited by examiner

*Primary Examiner* — David T Karst
(74) *Attorney, Agent, or Firm* — Oliff PLC

(57) ABSTRACT

An amine of the formula (I) and a process for its preparation by reductive alkylation of 1,2-propylenediamine with a di- or trifunctional carbonyl compound and hydrogen. The amine of the formula (I) is low in viscosity and in odour, high in reactivity towards epoxides and outstanding in its compatibility with other amines and with epoxy resins. The amine of the formula (I) allows access to low-emission epoxy resin compositions which have good processing qualities, cure rapidly even at low temperatures and form high-quality, high-hardness plastics having an attractive surface.

18 Claims, No Drawings

AMINE FOR LOW-EMISSION EPOXY RESIN COMPOSITIONS

TECHNICAL FIELD

The invention pertains to the field of amines, hardeners for epoxy resins, epoxy resin compositions, and their use, particularly as coating, covering or paint.

PRIOR ART

Epoxy resin compositions that are suitable for coating purposes are to have an extremely low viscosity so that they can be processed effectively at ambient temperature. They are also to cure very rapidly and without disruption, even under humid and cold conditions, while forming an even surface without hazing, speckling or craters. Lastly, a fully cured coating is to possess high hardness with low brittleness, in order to withstand mechanical stressing as effectively as possible. For optically demanding applications, such as top coverings on floors, for example, a coating, moreover, is to exhibit high gloss and as little as possible a tendency toward yellowing under the effect of light. Hardeners for epoxy resins that are based on the customary prior-art (cyclo)aliphatic polyamines such as isophoronediamine (IPDA), meta-xylylenediamine (MXDA) or trimethylhexamethylenediamine (TMD) in free form have a strong amine odor and, on account of their susceptibility to blushing effects, often result in severe curing defects, particularly when applied over a large area such as in coatings. "Blushing effects" are surface deficiencies which appear in the course of curing, such as hazing, speckles, roughness, and stickiness, and are caused by formation of salts ("blushing") between amines and carbon dioxide ($CO_2$) from the air, and occur particularly at high atmospheric humidity and low temperatures. In order to reduce the incidence of blushing effects, the polyamines used are typically subjected to partial preadducting with epoxides or epoxy resins. This, however, severely increases their viscosity and necessitates the use of diluents. The diluents lessen the blushing effects and enhance surface quality and coating brittleness, but are not incorporated into the resin matrix on curing and may be released by processes of evaporation or diffusion. Nowadays, however, the desire is increasingly for low-emission products which have a low content of releasable substances after curing. For low-emission epoxy resin compositions, therefore, diluents, such as benzyl alcohol, for example, can be used only in small quantities or not at all.

SUMMARY OF THE INVENTION

It is an object of the present invention, therefore, to provide a low-viscosity and low-odor amine with no tendency to blushing effects, which allows access to readily workable, low-emission epoxy resin compositions that cure rapidly and without defect.

This object is achieved by an amine of the formula (I) as claimed in claim 1. The amine of the formula (I) is low-odor and of surprisingly low viscosity in spite of the ring structure. Its reactivity toward $CO_2$ is so low that in air it shows no tendency either to form crusts or to exhibit precipitation or increases in viscosity. It has high reactivity toward epoxides and is outstandingly compatible with other amines and with epoxy resins. With the amine of the formula (I), it is possible to have access to low-emission epoxy resin compositions which are readily workable and which, even under adverse curing conditions, such as at 8° C., for example, cure rapidly to form high-quality plastics of high hardness and even, nontacky surface with high gloss.

Further aspects of the invention are subjects of the further independent claims. Particularly preferred embodiments of the invention are subjects of the dependent claims.

EMBODIMENTS OF THE INVENTION

A subject of the invention is an amine of the formula (I),

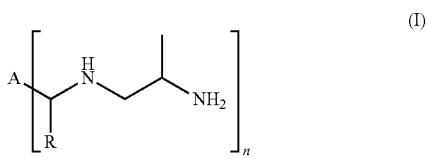

where
n is 2 or 3,
R is a hydrogen radical or is methyl or phenyl, and
A is an n-valent hydrocarbon radical having 5 to 20 C atoms which optionally contains oxygen or sulfur or nitrogen atoms and which comprises at least one cycloaliphatic or aromatic ring.

Substance names beginning with "poly", such as polyamine, polyol or polyepoxide, denote substances which formally contain per molecule two or more of the functional groups that occur in their name.

A "primary amino group" is an $NH_2$ group which is bonded to an organic radical, and a "secondary amino group" is an NH group which is bonded to two organic radicals, which may also together be part of a ring.

The "amine hydrogen" refers to the hydrogen atoms of primary and secondary amino groups.

"Amine hydrogen equivalent weight" is the weight fraction of a hardener or of an amine per amine hydrogen present in the hardener or amine.

An "unincorporable diluent" is a substance which is soluble in an epoxy resin and lowers its viscosity and which is not incorporated covalently into the resin matrix when the epoxy resin is cured.

The term "viscosity" in the present document refers to the dynamic viscosity or shear viscosity, which is defined by the ratio between the shearing stress and the shear rate (rate gradient) and is determined as described in the working examples.

A dashed line in the formulae in this document represents in each case the bond between a substituent and the remainder of the associated molecule.

"Molecular weight" is understood in the present document to be the molar mass (in grams per mole) of a molecule. "Average molecular weight" is the numerical average $M_n$ of an oligomeric or polymeric mixture of molecules, and is determined customarily by means of gel permeation chromatography (GPC) against polystyrene as standard.

"Room temperature" refers to a temperature of 23° C.

Preferably n is 2. These amines are of particularly low viscosity.

R is preferably a hydrogen radical. These amines are of particularly low viscosity and are particularly efficient to prepare.

Preferably A is free from hydroxyl groups. An amine of the formula (I) of this kind is of particularly low viscosity.

Preferably, A is an optionally substituted phenylene or cyclohexylene or dicycloheptylene or tricyclodecylene or pentacyclopentadecylene or furandiyl or tetrahydrofurandiyl or thiophenediyl or tetrahydrothiophenediyl or N,N'-piperazine-bis(2,2-dimethylpropane)diyl radical. These amines are particularly readily accessible.

More preferably A is a phenylene radical of the formula (IIa),

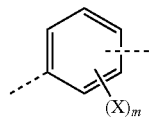

(IIa)

where
m is 0 or 1 or 2, and
X stands for identical or different radicals selected from the group consisting of alkyl and alkoxy having in each case 1 to 4 carbon atoms.

With further particular preference, A is a cyclohexylene radical of the formula (IIb) where m and X have the definitions already stated.

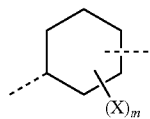

(IIb)

Preferably X is methyl or methoxy.
Preferably m is 0 or is 1. More preferably m is 0.
These amines of the formula (I) are of particularly low viscosity.

With further particular preference, A is a furan radical or is a thiophene radical of the formula (IIc) where Z is an oxygen atom or a sulfur atom.

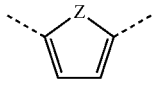

(IIc)

With further particular preference, A is a tetrahydrofuran radical or is a tetrahydrothiophene radical of the formula (IId) where Z has the definitions already stated.

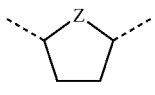

(IId)

With very particular preference, A is a 1,2- or 1,3- or 1,4-phenylene radical or is a 1,2- or 1,3- or 1,4-cyclohexylene radical.

More particularly A is a 1,4-phenylene radical or is a 1,4-cyclohexylene radical, most preferably a 1,4-phenylene radical.

The amine of the formula (I) is preferably selected from the group consisting of 1,2-bis(2-aminopropylaminomethyl)benzene, 1,3-bis(2-aminopropylaminomethyl)benzene, 1,4-bis(2-aminopropylaminomethyl)benzene, 1,2-bis(2-aminopropylaminomethyl)cyclohexane, 1,3-bis(2-aminopropylaminomethyl)cyclohexane, 1,4-bis(2-aminopropylaminomethyl)cyclohexane, 2(3),5(6)-bis(2-aminopropylaminomethyl)bicyclo[2.2.1]heptane, 3(4),8(9)-bis(2-aminopropylaminomethyl)tricyclo[5.2.1.02,6]decane, 4(5),11(12)-bis(2-aminopropylaminomethyl)pentacyclo[6.5.1.1$^{3,6}$.0$^{2,7}$.0$^{9,13}$]pentadecane, 6,12-bis(2-aminopropylaminomethyl)pentacyclo[9.2.1.1$^{5,8}$.0$^{4,9}$.0$^{2,10}$]pentadecane, 2,5-bis(2-aminopropylaminomethyl)furan, 2,5-bis(2-aminopropylaminomethyl)tetrahydrofuran, 2,5-bis(2-aminopropylaminomethyl)thiophene, 2,5-bis(2-aminopropylaminomethyl)tetrahydrothiophene, N,N'-bis((N-2-aminopropyl)-3-amino-2,2-dimethylpropyl)piperazine, 1,2-bis((N-2-aminopropyl)-1-aminoethyl)benzene, 1,3-bis((N-2-aminopropyl)-1-aminoethyl)benzene, 1,4-bis((N-2-aminopropyl)-1-aminoethyl)benzene, 1,2-bis((N-2-aminopropyl)-1-aminoethyl)cyclohexane, 1,3-bis((N-2-aminopropyl)-1-aminoethyl)cyclohexane, and 1,4-bis((N-2-aminopropyl)-1-aminoethyl)cyclohexane.

Preferred among these are 1,2-bis(2-aminopropylaminomethyl)benzene, 1,3-bis(2-aminopropylaminomethyl)benzene, 1,4-bis(2-aminopropylaminomethyl)-benzene, 1,2-bis(2-aminopropylaminomethyl)cyclohexane, 1,3-bis(2-aminopropylaminomethyl)cyclohexane, 1,4-bis(2-aminopropylaminomethyl)cyclohexane, 1,4-bis((N-2-aminopropyl)-1-aminoethyl)benzene or 1,4-bis((N-2-aminopropyl)-1-aminoethyl)cyclohexane.

Particularly preferred is 1,4-bis(2-aminopropylaminomethyl)benzene or 1,4-bis-(2-aminopropylaminomethyl)cyclohexane, especially 1,4-bis(2-aminopropylaminomethyl)benzene.

The preferred amines of the formula (I) are notable for particularly low viscosity and good properties in their use as hardeners for epoxy resins.

An amine of the formula (I) may be obtained with particular advantage through reductive alkylation of 1,2-propylenediamine with a di- or trifunctional carbonyl compound of the formula (III) and hydrogen. The reaction product from this preparation is particularly suitable as a hardener for epoxy resins in the manner described.

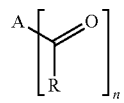

(III)

In the formula (III), n, R and A have the definitions already stated.

A further subject of the invention, accordingly, is a process for preparing an amine of the formula (I) by reductive alkylation of 1,2-propylenediamine with at least one di- or trifunctional carbonyl compound of the formula (III) and hydrogen.

The reductive alkylation may take place directly with molecular hydrogen or indirectly by hydrogen transfer from other reagents, such as formic acid, for example. With preference, molecular hydrogen is used. In this case, the conditions are advantageously selected such that mainly one primary amino group in each case of 1,2-propylenediamine is singly alkylated with high selectivity and therefore two or three 1,2-propylenediamine molecules and the carbonyl compound of the formula (III) combine to form an amine of the formula (I). If the carbonyl compound of the formula (III) contains a radical A having an aromatic ring, this ring, depending on the setting of the reaction conditions for the reductive alkylation, may remain unhydrogenated or may be deliberately hydrogenated as well.

The reaction is carried out preferably at a temperature of 40 to 120° C. and in the presence of a suitable catalyst. Preferred as catalyst are palladium on carbon (Pd/C), platinum on carbon (Pt/C), Adams catalyst or Raney nickel, more particularly palladium on carbon or Raney nickel.

When using molecular hydrogen, operation takes place preferably in a pressurized apparatus under a hydrogen pressure of 5 to 250 bar, more particularly 10 to 100 bar.

One preferred embodiment of the preparation uses 1,2-propylenediamine in stoichiometric excess over the carbonyl groups of the carbonyl compound of the formula (III). The ratio between the number of 1,2-propylenediamine molecules and the number of carbonyl groups is preferably at least 2/1, more particularly at least 3/1, more preferably at least 4/1. The excess 1,2-propylenediamine is removed, in particular by distillation, before or—preferably—after the reduction.

Preparing the amine of the formula (I) by reductive alkylation in the manner described is particularly advantageous for use as hardener for epoxy resins, because primary amino groups are singly alkylated with high selectivity, whereas secondary amino groups are barely alkylated further. Amines of the formula (I) prepared in this way are particularly pure, have particularly low viscosity, and can be used without further work-up as hardeners for epoxy resins. The product from the preparation process described can therefore be used without further processing for curing epoxy resins in the manner described.

Depending on reaction conditions during the preparation, the product after the preparation may contain byproducts as well as the amine of the formula (I). Present in particular may be oligomeric compounds from the dialkylation of 1,2-propylenediamine. Such oligomeric compounds lead to an increase in the viscosity of the reaction product. The preparation is preferably conducted such that the formation of oligomeric compounds is suppressed as far as possible. Other byproducts that may be present are 1,2-propylenediamines alkylated on the less-reactive amino group, such as, for example, diamines of the formula

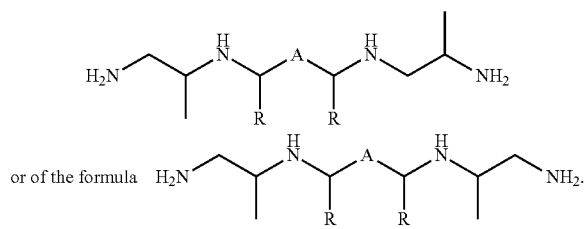

or of the formula

Suitability as carbonyl compound of the formula (III) is possessed in particular by
dialdehydes, especially ortho-phthalaldehyde (1,2-benzenedicarbaldehyde), isophthalaldehyde (1,3-benzenedicarbaldehyde), terephthalaldehyde (1,4-benzenedicarbaldehyde), naphthalenedicarboxaldehyde, anthracenedicarboxaldehyde, 2,5-furandicarbaldehyde, 2,5-thiophenedicarbaldehyde, cyclopentanedicarbaldehyde, 1,2-cyclohexanedicarbaldehyde, 1,3-cyclohexanedicarbaldehyde, 1,4-cyclohexanedicarbaldehyde, 2(3),5(6)-diformylbicyclo[2.2.1]heptane (norbornanedicarbaldehyde), 3(4),8(9)-diformyltricyclo[5.2.1.0$^{2,6}$]decane (tricyclodecanedicarbaldehyde or TCD-dialdehyde), 4(5),11(12)-diformylpentacyclo[6.5.1.1$^{3,6}$.0$^{2,7}$.0$^{9,13}$]pentadecane and/or 6,12-diformylpentacyclo[9.2.1.1$^{5,8}$.0$^{4,9}$.0$^{2,10}$]pentadecane (pentacyclopentadecanedicarbaldehyde), 2,5-tetrahydrofurandicarbaldehyde, 2,5-tetrahydrothiophenedicarbaldehyde, 1,3-bis(4,4-dimethyl-5-oxo-2-pentyl)benzene, 1,4-bis(4,4-dimethyl-5-oxo-2-pentyl)benzene, 3-(3-oxopropyl) cyclohexanecarbaldehyde, 4-(3-oxopropyl) cyclohexanecarbaldehyde, 3-(1-formylethyl) cyclohexanecarbaldehyde, 4-(1-formylethyl) cyclohexanecarbaldehyde, N,N'-bis(2,2-dimethyl-3-oxopropyl)piperazine, N,N'-bis(2,2-diethyl-3-oxopropyl)piperazine, N,N'-bis(2-methyl-2-propyl-3-oxopropyl)piperazine or N,N'-bis(2-butyl-2-ethyl-3-oxopropyl)piperazine;

trialdehydes, especially 1,3,5-benzenetricarbaldehyde or 1,3,5-cyclohexanetricarbaldehyde;

diketones, especially 1,2-diacetylbenzene, 1,3-diacetylbenzene, 1,4-diacetylbenzene, 1,2-diacetylcyclohexane, 1,3-diacetylcyclohexane or 1,4-diacetylcyclohexane;

triketones, especially 1,3,5-triacetylbenzene or 1,3,5-triacetylcyclohexane; or ketoaldehydes, especially 2-acetylbenzaldehyde, 3-acetylbenzaldehyde or 4-acetylbenzaldehyde.

Preference is given to the dialdehydes, especially ortho-phthalaldehyde, isophthalaldehyde, terephthalaldehyde, 2,5-furandicarbaldehyde, 2,5-thiophenedicarbaldehyde, 1,2-cyclohexanedicarbaldehyde, 1,3-cyclohexanedicarbaldehyde, 1,4-cyclohexanedicarbaldehyde, norbornanedicarbaldehyde, TCD dialdehyde, pentacyclopentadecanedicarbaldehyde or N,N'-bis(2,2-dimethyl-3-oxopropyl)piperazine, and also the diketones, especially 1,2-diacetylbenzene, 1,3-diacetylbenzene, 1,4-diacetylbenzene, 1,2-diacetylcyclohexane, 1,3-diacetylcyclohexane or 1,4-diacetylcyclohexane.

Particularly preferred are ortho-phthalaldehyde, isophthalaldehyde, terephthalaldehyde, 1,2-cyclohexanedicarbaldehyde, 1,3-cyclohexanedicarbaldehyde, 1,4-cyclohexanedicarbaldehyde, 1,4-diacetylbenzene or 1,4-diacetylcyclohexane.

Most preferred are terephthalaldehyde or 1,4-cyclohexanedicarbaldehyde, especially terephthalaldehyde.

It may be advantageous to use distillation to purify the reaction product from the preparations described. In this way it is possible to remove unreacted 1,2-propylenediamine and/or oligomeric byproducts from the reaction mixture.

The amine of the formula (I) is a low-odor substance which in spite of the ring structure has a surprisingly low viscosity. It has such a low reactivity toward $CO_2$ that—in contrast to many prior-art amines—it shows no tendency in air either to form crusts or to exhibit precipitation or increase in viscosity. It has a high reactivity for epoxides and exhibits excellent compatibility with other amines and with epoxy resins, and is therefore particularly suitable for use as a hardener for epoxy resins.

A further subject of the invention, accordingly, is the use of an amine of the formula (I) as hardener for epoxy resins.

In particular a reaction product from the reductive alkylation of 1,2-propylenediamine with a di- or trifunctional carbonyl compound of the formula (III) and hydrogen, as described above, is used as hardener for epoxy resins. A reaction product of this kind is easy to obtain and contains a high fraction of amine of the formula (I).

A reaction product of this kind, in addition to the amine of the formula (I), typically also includes fractions alkylated on the $N^2$ nitrogen of 1,2-propylenediamine, such as, for example, 1-(2-aminopropylaminomethyl)-4-(1-aminoprop-2-ylaminomethyl)benzene, 1,4-bis(1-aminoprop-2-ylaminomethyl)benzene, 1-(2-aminopropylaminomethyl)-4-(1-aminoprop-2-ylaminomethyl)cyclohexane, 1,4-bis(1-aminoprop-2-ylaminomethyl)cyclohexane, or oligomeric reaction products.

A further subject of the invention is a hardener for epoxy resins, comprising at least one amine of the formula (I) and at least one further amine and/or at least one accelerator. The further amine in this case is not an amine of the formula (I). A hardener of this kind has particularly low viscosity and/or particularly high reactivity toward epoxy resins.

Suitable accelerators are substances which accelerate the reaction between amino groups and epoxide groups, more particularly acids or compounds which can be hydrolyzed to acids, more particularly organic carboxylic acids such as acetic acid, benzoic acid, salicylic acid, 2-nitrobenzoic acid, lactic acid, organic sulfonic acids such as methanesulfonic acid, p-toluenesulfonic acid or 4-dodecylbenzenesulfonic acid, sulfonic esters, other organic or inorganic acids such as, in particular, phosphoric acid, or mixtures of the aforementioned acids and acid esters; tertiary amines such as, in particular, 1,4-diazabicyclo-[2.2.2]octane, benzyldimethylamine, α-methylbenzyldimethylamine, triethanolamine, dimethylaminopropylamine, imidazoles such as, in particular, N-methylimidazole, N-vinylimidazole or 1,2-dimethylimidazole, salts of such tertiary amines, quaternary ammonium salts, such as, in particular benzyltrimethylammonium chloride, amidines such as, in particular, 1,8-diazabicyclo [5.4.0]-undec-7-ene, guanidines such as, in particular, 1,1,3,3-tetramethylguanidine, phenols, especially bisphenols, phenolic resins or Mannich bases such as, in particular, 2-(dimethylaminomethyl)phenol, 2,4,6-tris(dimethylaminomethyl)-phenol or polymers of phenol, formaldehyde and N,N-dimethyl-1,3-propanediamine, phosphites such as, in particular, diphenyl or triphenyl phosphites, or compounds containing mercapto groups. Preferred accelerators are acids, tertiary amines or Mannich bases.

Most preferred is salicylic acid or 2,4,6-tris(dimethylaminomethyl)phenol or a combination thereof.

Especially suitable as further amine are polyamines which have at least two, more particularly at least three, amine hydrogens reactive toward epoxide groups, more particularly the following polyamines:

reaction products from the reductive alkylation of 1,2-propylenediamine with a di- or trifunctional carbonyl compound of the formula (III) and hydrogen that are not of the formula (I), more particularly 1-(2-aminopropylaminomethyl)-4-(1-aminoprop-2-ylaminomethyl)benzene, 1,4-bis(1-aminoprop-2-ylaminomethyl) benzene, 1-(2-aminopropylaminomethyl)-4-(1-aminoprop-2-ylaminomethyl)cyclohexane, 1,4-bis(1-aminoprop-2-ylaminomethyl)cyclohexane or oligomeric reaction products;

aliphatic, cycloaliphatic or arylaliphatic primary diamines, especially 2,2-dimethyl-1,3-propanediamine, 1,3-pentanediamine (DAMP), 1,5-pentanediamine, 1,5-diamino-2-methylpentane (MPMD), 2-butyl-2-ethyl-1,5-pentanediamine (C11-neodiamine), 1,6-hexanediamine, 2,5-dimethyl-1,6-hexanediamine, 2,2(4),4-trimethylhexamethylenediamine (TMD), 1,7-heptanediamine, 1,8-octanediamine, 1,9-nonanediamine, 1,10-decanediamine, 1,11-undecanediamine, 1,12-dodecanediamine, 1,2-, 1,3- or 1,4-diaminocyclohexane, bis(4-aminocyclohexyl)methane ($H_{12}$-MDA), bis(4-amino-3-methylcyclohexyl)methane, bis(4-amino-3-ethylcyclohexyl)methane, bis(4-amino-3,5-dimethylcyclohexyl)methane, bis(4-amino-3-ethyl-5-methylcyclohexyl)methane, 1-amino-3-aminomethyl-3,5,5-trimethylcyclohexane (isophoronediamine or IPDA), 2- or 4-methyl-1,3-diaminocyclohexane or mixtures thereof, 1,3-bis(aminomethyl)cyclohexane, 1,4-bis(aminomethyl)cyclohexane, 2,5(2,6)-bis(aminomethyl)bicyclo[2.2.1] heptane (NBDA), 3(4),8(9)-bis(aminomethyl)tricyclo[5.2.1.0$^{2,6}$]decane, 1,4-diamino-2,2,6-trimethylcyclohexane (TMCDA), 1,8-menthanediamine, 3,9-bis(3-aminopropyl)-2,4,8,10-tetraoxaspiro[5.5]undecane, 1,3-bis(aminomethyl) benzene (MXDA) or 1,4-bis(aminomethyl)benzene;

aliphatic, cycloaliphatic or arylaliphatic primary triamines, especially 4-aminomethyl-1,8-octanediamine, 1,3,5-tris(aminomethyl)benzene, 1,3,5-tris(aminomethyl)cyclohexane, tris(2-aminoethyl)amine, tris(2-aminopropyl)amine or tris(3-aminopropyl)amine;

aliphatic primary di- or triamines containing ether groups, especially bis(2-aminoethyl) ether, 3,6-dioxaoctane-1,8-diamine, 4,7-dioxadecane-1,10-diamine, 4,7-dioxadecane-2,9-diamine, 4,9-dioxadodecane-1,12-diamine, 5,8-dioxadodecane-3,10-diamine, 4,7,10-trioxatridecane-1,13-diamine or higher oligomers of these diamines, bis(3-aminopropyl)polytetrahydrofurans or other polytetrahydrofurandiamines, cycloaliphatic ether group-containing diamines from the propoxylation and subsequent amination of 1,4-dimethylolcyclohexane, obtainable in particular as Jeffamine® RFD-270 (from Huntsman), or polyoxyalkylenedi- or -triamines, which typically represent products from the amination of polyoxyalkylenedi- or -triols and are obtainable, for example, under the name Jeffamine® (from Huntsman), under the name Polyetheramine (from BASF) or under the name PC Amine® (from Nitroil). Especially suitable polyoxyalkylenedi- or -triamines are Jeffamine® D-230, Jeffamine® D-400, Jeffamine® D-2000, Jeffamine® EDR-104, Jeffamine® EDR-148, Jeffamine® EDR-176, Jeffamine® T-403, Jeffamine® T-3000, Jeffamine® T-5000, or corresponding amines from BASF or Nitroil;

polyamines containing secondary amino groups having two primary aliphatic amino groups, such as, in particular, 3-(2-aminoethyl)aminopropylamine, bis(hexamethylene)triamine (BHMT), diethylenetriamine (DETA), triethylenetetramine (TETA), tetraethylenepentamine (TEPA), pentaethylenehexamine (PEHA) or higher homologs of linear polyethyleneamines such as polyethylenepolyamine having 5 to 7 ethyleneamine units (referred to as "higher ethylenepolyamine", HEPA), products from the multiple cyanoethylation or cyanobutylation and subsequent hydrogenation of primary di- and polyamines having at least two primary amino groups, such as dipropylenetriamine (DPTA), N-(2-aminoethyl)-1,3-propanediamine (N3-amine), N,N'-bis(3-aminopropyl)-ethylenediamine (N4-amine), N,N'-bis(3-aminopropyl)-1,4-diaminobutane, N5-(3-aminopropyl)-2-methyl-1,5-pentanediamine, N3-(3-aminopentyl)-1,3-pentanediamine, N5-(3-amino-1-ethylpropyl)-2-methyl-1,5-pentanediamine or N,N'-bis(3-amino-1-ethylpropyl)-2-methyl-1,5-pentanediamine;

polyamines having one or two secondary amino groups, especially products from the reductive alkylation of primary aliphatic polyamines with monofunctional aldehydes or ketones, especially N-benzyl-1,3-bis (aminomethyl)-benzene, N,N'-dibenzyl-1,3-bis(aminomethyl)benzene, N-2-ethylhexyl-1,3-bis(aminomethyl)benzene, N,N'-bis(2-ethylhexyl)-1,3-bis(aminomethyl)-benzene, N-benzyl-1,2-propanediamine, N-(4-methoxybenzyl)-1,2-propanediamine, N-(4-(dimethylamino)benzyl)-1,2-propanediamine, N-(1-phenylethyl)-1,2-propanediamine, N-benzhydryl-1,2-propanediamine, N-(1-(4'-methyl)phenylethyl)-1,2-propanediamine, N-(1-(4'-methoxy)phenylethyl)-1,2-propanediamine, or partially styrenized polyamines such as, for example, styrenized MXDA (available as Gaskamine® 240 from Mitsubishi Gas Chemical);

aromatic polyamines, such as, in particular, m- and p-phenylenediamine, 4,4'-, 2,4' and/or 2,2'-diaminodiphenylmethane, 3,3'-dichloro-4,4'-diaminodiphenylmethane (MOCA), 2,4- and/or 2,6-tolylenediamine, mixtures of 3,5-dimethylthio-2,4- and -2,6-tolylenediamine (available as Ethacure® 300 from Albermarle), mixtures of 3,5-diethyl-2,4- and -2,6-tolylenediamine (DETDA), 3,3',5,5'-tetraethyl-4,4'-diaminodiphenylmethane (M-DEA), 3,3',5,5'-tetraethyl-2,2'-dichloro-4,4'-diaminodiphenylmethane (M-CDEA), 3,3'-diisopropyl-5,5'-dimethyl-4,4'-diaminodiphenylmethane (M-MIPA), 3,3',5,5'-tetraisopropyl-4,4'-diaminodiphenylmethane (M-DIPA), 4,4'-diaminodiphenyl sulfone (DDS), 4-amino-N-(4-aminophenyl)benzenesulfonamide, 5,5'-methylenedianthranilic acid, dimethyl 5,5'-methylenedianthranilate, 1,3-propylene bis(4-aminobenzoate), 1,4-butylene bis(4-aminobenzoate), polytetramethylene oxide bis(4-aminobenzoate) (available as Versalink® from Air Products), 1,2-bis(2-aminophenylthio)ethane, 2-methylpropyl 4-chloro-3,5-diaminobenzoate or tert-butyl (4-chloro-3,5-diaminobenzoate);

adducts of the stated polyamines with epoxides or epoxy resins, especially adducts with diepoxides having a molar ratio of approximately 2/1, adducts with monoepoxides having a molar ratio of approximately 1/1, or reaction products of amines and epichlorohydrin, more particularly that of 1,3-bis(aminomethyl)benzene, available commercially as Gaskamine® 328 (from Mitsubishi Gas Chemical);

polyamidoamines, especially reaction products of a mono- or polybasic carboxylic acid, and/or the esters or anhydrides thereof, particularly of a dimer fatty acid, with an aliphatic, cycloaliphatic or aromatic polyamine that is used in a stoichiometric excess, more particularly a polyalkyleneamine such as, for example, DETA or TETA, more particularly the commercially available polyamidoamines Versamid® 100, 125, 140 or 150 (from Cognis), Aradur® 223, 250 or 848 (from Huntsman), Euretek® 3607 or 530 (from Huntsman) or Beckopox® EH 651, EH 654, EH 655, EH 661 or EH 663 (from Cytec); or phenalkamines, also called Mannich bases, especially reaction products of a Mannich reaction of phenols, more particularly cardanol, with aldehydes, more particularly formaldehyde, especially the commercially available phenalkamines Cardolite® NC-541, NC-557, NC-558, NC-566, Lite 2001 or Lite 2002 (from Cardolite), Aradur® 3440, 3441, 3442 or 3460 (from Huntsman) or Beckopox® EH 614, EH 621, EH 624, EH 628 or EH 629 (from Cytec).

Preferred as further amine are reaction products from the reductive alkylation of 1,2-propylenediamine with a di- or trifunctional carbonyl compound of the formula (III) and hydrogen that are not of the formula (I), more particularly 1-(2-aminopropylaminomethyl)-4-(1-aminoprop-2-ylaminomethyl)benzene, 1,4-bis(1-aminoprop-2-ylaminomethyl)benzene, 1-(2-aminopropylaminomethyl)-4-(1-aminoprop-2-ylaminomethyl)cyclohexane, 1,4-bis(1-aminoprop-2-ylaminomethyl)cyclohexane or oligomeric reaction products.

Preferred as further amine are also partially styrenized polyamines, especially partially styrenized MXDA, or products from the reductive alkylation of primary aliphatic polyamines with monofunctional aldehydes or ketones, especially those of 1,2-propylenediamine such as, in particular, N-benzyl-1,2-propanediamine, N-(4-methoxybenzyl)-1,2-propanediamine, N-(4-(dimethylamino)benzyl)-1,2-propanediamine, N-(1-phenylethyl)-1,2-propanediamine, N-benzhydryl-1,2-propanediamine, N-(1-(4'-methyl)phenylethyl)-1,2-propanediamine or N-(1-(4'-methoxy)phenylethyl)-1,2-propanediamine.

Preferred as further amine, moreover, are ether group-containing aliphatic primary di- or triamines, more particularly polyoxyalkylene di- or -triamines having an average molecular weight in the range from 200 to 500 g/mol, especially Jeffamine® D-230 or Jeffamine® T-403 (both from Huntsman), or cycloaliphatic ether group-containing diamines from the propoxylation and subsequent amination of 1,4-dimethylolcyclohexane, especially Jeffamine® RFD-270 (from Huntsman). An amine of this kind allows access to epoxy resin compositions with a reliable curing to high ultimate hardness without so-called "freezing" and with low brittleness after curing. "Freezing" refers to the phenomenon whereby, after initially good development of hardness, an epoxy resin composition fails to cure to the anticipated ultimate hardness at a given temperature, the curing instead remaining at a relatively low hardness. Such effects occur in particular at low curing temperatures.

Additionally preferred as further amine are an adduct of (i) at least one polyamine, having at least three amine hydrogens reactive toward epoxide groups, with (ii) at least one epoxide.

Preferred as polyamine for such an adduct are the aforementioned polyamines having at least three amine hydrogens that are reactive toward epoxide groups, or smaller polyamines such as, in particular, ethylenediamine, the isomeric propylenediamines or the isomeric butylenediamines.

Preferred as epoxide for such an adduct are diepoxides or monoepoxides, especially aromatic monoepoxides such as especially cresyl glycidyl ether, tert-butylphenyl glycidyl ether or the glycidyl ether of cardanol. Particularly preferred is cresyl glycidyl ether. Suitable cresyl glycidyl ethers are all isomeric cresyl glycidyl ethers or mixtures thereof, more particularly commercially available types such as, in particular, Araldite® DY-K (from Huntsman), Polypox™ R6 (from Dow), Heloxy™ KR (from Hexion) or Erisys® GE-10 (from CVC Spec. Chem.).

The adduct is prepared preferably by slow metered addition of the epoxide to an initial charge of polyamine, the temperature of the reactants being maintained preferably in the range from 40 to 120° C., more particularly 50 to 110° C.

A preferred adduct is an adduct of 1,2-propylenediamine with cresyl glycidyl ether that is especially prepared with an excess of 1,2-propylenediamine and with subsequent removal of the excess by distillation.

A further preferred adduct is an adduct of 1,5-diamino-2-methylpentane with cresyl glycidyl ether especially one that has either been prepared with an excess of 1,5-diamino- 2-methylpentane, with subsequent removal of the excess by distillation, or with a slight excess of cresyl glycidyl ether.

A further preferred adduct is an adduct of 2,2(4),4-trimethylhexamethylenediamine with cresyl glycidyl ether that is especially prepared with a slight excess of 2,2(4),4-trimethylhexamethylenediamine.

The term "excess" in this case relates not to the reactive groups but rather to the molar ratio between the polyamine molecule and the monoepoxy molecule. These preferred adducts are of comparatively low viscosity, exhibit particularly high compatibility and reactivity with the customary epoxy resin compositions and enable fully cured films of high gloss and high hardness to be produced.

The hardener of the invention comprises preferably 1 to 95 weight %, more preferably 2 to 90 weight %, more particularly 5 to 80 weight %, of amine of the formula (I).

Hardeners of this kind are notable for low viscosity and allow access to epoxy resin coatings having high cure rate, hardly any tendency toward blushing effects, and high hardness.

The hardener typically comprises a certain fraction of products alkylated on the $N^2$ nitrogen—in the case of 1,4-bis(2-aminopropylaminomethyl)benzene, for example, a certain fraction of 1-(2-aminopropylaminomethyl)-4-(1-aminoprop-2-ylaminomethyl)benzene and/or 1,4-bis(1-aminoprop-2-ylaminomethyl)benzene.

The hardener is preferably largely free of 1,2-propylenediamine. More particularly it contains less than 1 weight %, more preferably less than 0.1 weight %, of 1,2-propylenediamine.

With further preference the hardener is largely free from amines having a molecular weight below 120 g/mol, more particularly below 150 g/mol. The hardener contains preferably less than 2 weight %, more particularly less than 1 weight %, of amines having a molecular weight below 120 g/mol, more particularly below 150 g/mol.

A hardener of this kind has particularly toxicological and odor advantages and enables access to coatings having particularly attractive surfaces.

The hardener may further comprise at least one unincorporable diluent, more particularly xylene, 2-methoxyethanol, dimethoxyethanol, 2-ethoxyethanol, 2-propoxyethanol, 2-isopropoxyethanol, 2-butoxyethanol, 2-phenoxyethanol, 2-benzyloxyethanol, benzyl alcohol, ethylene glycol, ethylene glycol dimethyl ether, ethylene glycol diethyl ether, ethylene glycol dibutyl ether, ethylene glycol diphenyl ether, diethylene glycol, diethylene glycol monomethyl ether, diethylene glycol monoethyl ether, diethylene glycol mono-n-butyl ether, diethylene glycol dimethyl ether, diethylene glycol diethyl ether, diethylene glycol di-n-butylyl ether, propylene glycol butyl ether, propylene glycol phenyl ether, dipropylene glycol, dipropylene glycol monomethyl ether, dipropylene glycol dimethyl ether, dipropylene glycol di-n-butyl ether, N-methylpyrrolidone, diphenylmethane, diisopropylnaphthalene, petroleum fractions such as, for example, Solvesso® grades (from Exxon), alkylphenols such as tert-butylphenol, nonylphenol, dodecylphenol and 8,11,14-pentadecatrienylphenol (Cardanol, from cashew shell oil, available for example as Cardolite NC-700 from Cardolite Corp., USA), styrenized phenol, bisphenols, aromatic hydrocarbon resins, especially those containing phenol groups, alkoxylated phenol, especially ethoxylated or propoxylated phenol, more particularly 2-phenoxyethanol, adipates, sebacates, phthalates, benzoates, organic phosphoric acid esters or sulfonic acid esters or sulfonamides. Preferred are benzyl alcohol, dodecylphenol, tert-butylphenol, styrenized phenol, ethoxylated phenol, or aromatic hydrocarbon resins containing phenol groups, more particularly the Novares® grades LS 500, LX 200, LA 300 or LA 700 (from Rütgers).

The hardener preferably contains none or only a low level of unincorporable diluents. With preference the hardener contains not more than 10 weight %, especially not more than 5 weight %, of unincorporable diluents.

The hardener may comprise further substances that are reactive toward epoxide groups, examples being monoamines such as hexylamine or benzylamine, or compounds containing mercapto groups, more particularly the following:

liquid, mercaptan-terminated polysulfide polymers, known under the brand name Thiokol® (from Morton Thiokol; available for example from SPI Supplies, or from Toray Fine Chemicals), more particularly types LP-3, LP-33, LP-980, LP-23, LP-55, LP-56, LP-12, LP-31, LP-32 or LP-2; and also, moreover, under the brand name Thioplast® (from Akzo Nobel), more particularly the types G 10, G 112, G 131, G 1, G 12, G 21, G 22, G 44 or G 4;

mercaptan-terminated polyoxyalkylene ethers, available for example by reaction of polyoxyalkylenediols or -triols either with epichlorohydrin or with an alkylene oxide, followed by sodium hydrogensulfide;

mercaptan-terminated compounds in the form of polyoxyalkylene derivatives known under the brand name Capcure® (from Cognis), especially types WR-8, LOF or 3-800;

polyesters of thiocarboxylic acids, for example pentaerythritol tetramercaptoacetate, trimethylolpropane trimercaptoacetate, glycol di mercaptoacetate, pentaerythritol tetra(3-mercaptopropionate), trimethylolpropane tri(3-mercaptopropionate) or glycol di-(3-mercaptopropionate), or products of esterification of polyoxyalkylenediols or -triols, of ethoxylated trimethylolpropane or of polyester diols with thiocarboxylic acids such as thioglycolic acid or 2- or 3-mercaptopropionic acid; or further compounds containing mercapto groups, such as, in particular, 2,4,6-trimercapto-1,3,5-triazine, 2,2'-(ethylenedioxy)diethanethiol (triethylene glycol dimercaptan) or ethanedithiol.

A further subject of the invention is an epoxy resin composition comprising a resin component comprising at least one epoxy resin and a hardener component comprising at least one amine of the formula (I) as described above.

The hardener component preferably comprises a hardener comprising at least one amine of the formula (I) and at least one further amine and/or at least one accelerator, as described above.

Suitability as epoxy resin is possessed by customary technical epoxy resins. These are obtained in a known manner, as for example from the oxidation of the corresponding olefins or from the reaction of epichlorohydrin with the corresponding polyols, polyphenols or amines.

Particularly suitable as epoxy resin are what are called liquid polyepoxy resins, referred to hereinafter as "liquid resin". These have a glass transition temperature below 25° C.

Likewise possible as epoxy resin are what are called solid resins, which have a glass transition temperature above 25° C. and can be comminuted to powders which are pourable at 25° C.

Suitable epoxy resins are, in particular, aromatic epoxy resins, more particularly the glycidylization products of:

bisphenol A, bisphenol F or bisphenol A/F, where A stands for acetone and F for formaldehyde, which served as reactants in the preparation of these bisphenols. In the case of bisphenol F, there may also be positional isomers present, derived more particularly from 2,4'- or 2,2'-hydroxyphenylmethane.

dihydroxybenzene derivatives such as resorcinol, hydroquinone or pyrochatechol;

further bisphenols or polyphenols such as bis(4-hydroxy-3-methylphenyl)methane, 2,2-bis(4-hydroxy-3-methylphenyl)propane (bisphenol C), bis-(3,5-dimethyl-4-hydroxyphenyl)methane, 2,2-bis(3,5-dimethyl-4-hydroxyphenyl)propane, 2,2-bis(3,5-dibromo-4-hydroxyphenyl)propane, 2,2-bis(4-hydroxy-3-tert-butylphenyl)propane, 2,2-bis(4-hydroxyphenyl)butane (bisphenol B), 3,3-bis(4-hydroxyphenyl)pentane, 3,4-bis(4-hydroxyphenyl)hexane, 4,4-bis(4-hydroxyphenyl)heptane, 2,4-bis(4-hydroxyphenyl)-2-methylbutane, 2,4-bis(3,5-dimethyl-4-hydroxyphenyl)-2-methylbutane, 1,1-bis(4-hydroxyphenyl)cyclohexane (bisphenol Z), 1,1-bis(4-hydroxyphenyl)-3,3,5-trimethylcyclohexane (bisphenol-TMC), 1,1-bis(4-hydroxyphenyl)-1-phenylethane, 1,4-bis[2-(4-hydroxyphenyl)-2-propyl]benzene (bisphenol P), 1,3-bis[2-(4-hydroxyphenyl)-2-propyl]benzene (bisphenol M), 4,4'-dihydroxybiphenyl (DOD), 4,4'-dihydroxybenzophenone, bis(2-hydroxynaphth-1-yl)methane, bis(4-hydroxynaphth-1-yl)methane, 1,5-dihydroxynaphthalene, tris(4-hydroxyphenyl)methane, 1,1,2,2-tetrakis(4-hydroxyphenyl)ethane, bis(4-hydroxyphenyl) ether or bis(4-hydroxyphenyl) sulfone;

condensation products of phenols with formaldehyde which are obtained under acidic conditions, such as phenol novolaks or cresol novolaks, also called bisphenol F novolaks;

aromatic amines, such as aniline, toluidine, 4-aminophenol, 4,4'-methylenediphenyldiamine, 4,4'-methylenediphenyldi-(N-methyl)amine, 4,4'-[1,4-phenylenebis(1-methylethylidene)]bisaniline (bisaniline P) or 4,4'-[1,3-phenylenebis(1-methylethylidene)]bisaniline (bisaniline M).

Further suitable epoxy resins are aliphatic or cycloaliphatic polyepoxides, more particularly glycidyl ethers of saturated or unsaturated, branched or unbranched, cyclic or open-chain di-, tri- or tetra-functional $C_2$ to $C_{30}$ alcohols, especially ethylene glycol, propylene glycol, butylene glycol, hexanediol, octanediol, polypropylene glycols, dimethylolcyclohexane, neopentyl glycol, dibromoneopentyl glycol, castor oil, trimethylolpropane, trimethylolethane, pentaerythritol, sorbitol or glycerol, or alkoxylated glycerol or alkoxylated trimethylolpropane;

a hydrogenated bisphenol A, F or A/F liquid resin, or the glycidylation products of hydrogenated bisphenol A, F or A/F;

a N-glycidyl derivative of amides or heterocyclic nitrogen bases, such as triglycidyl cyanurate or triglycidyl isocyanurate, or reaction products of epichlorohydrin with hydantoin.

epoxy resins from the oxidation of olefins, such as, in particular, vinylcyclohexene, dicyclopentadiene, cyclohexadiene, cyclododecadiene, cyclododecatriene isoprene, 1,5-hexadiene, butadiene, polybutadiene or divinylbenzene.

A preferred epoxy resin in the resin component is a liquid resin based on a bisphenol, more particularly a diglycidyl ether of bisphenol A, bisphenol F or bisphenol A/F, of the kind available commercially, for example, from Dow, Huntsman or Momentive. These liquid resins have a low viscosity for epoxy resins and in the cured state exhibit good properties as a coating. They may include fractions of solid bisphenol A resin or bisphenol F novolaks.

The resin component may comprise are active diluent, more particularly a reactive diluent having at least one epoxide group. Particularly suitable as reactive diluents are the glycidyl ethers of mono- or polyhydric phenols or aliphatic or cycloaliphatic alcohols, such as, in particular, the aforementioned polyglycidyl ethers of di- or polyols, or, furthermore, phenyl glycidyl ether, cresyl glycidyl ether, benzyl glycidyl ether, p-n-butylphenyl glycidyl ether, p-tert-butylphenyl glycidyl ether, nonylphenyl glycidyl ether, allyl glycidyl ether, butyl glycidyl ether, hexyl glycidyl ether, 2-ethylhexyl glycidyl ether, or glycidyl ethers of natural alcohols such as, in particular, $C_8$ to $C_{10}$ alkyl glycidyl ether or $C_{12}$ to $C_{14}$ alkyl glycidyl ether. The addition of a reactive diluent to the epoxy resin has the effect of reducing the viscosity, and/or of reducing the glass transition temperature and/or the mechanical values.

The epoxy resin composition optionally comprises further constituents, particularly auxiliaries and adjuvants customarily used in epoxy resin compositions, examples being the following:

solvents, diluents, film-forming assistants or extenders, such as especially the aforementioned unincorporable diluents;

reactive diluents, especially reactive diluents containing epoxide groups, as mentioned above, epoxidized soybean oil or linseed oil, compounds containing acetoacetate groups, especially acetoacetylated polyols, butyrolactone, carbonates, aldehydes, and also, moreover, isocyanates or silicones containing reactive groups;

polymers, especially polyamides, polysulfides, polyvinylformal (PVF), polyvinylbutyral (PVB), polyurethanes (PU), polymers with carboxyl groups, polyam ides, butadiene-acrylonitrile copolymers, styrene-acrylonitrile copolymers, butadiene-styrene copolymers, homo- or copolymers of unsaturated monomers, especially from the group encompassing ethylene, propylene, butylene, isobutylene, isoprene, vinyl acetate or alkyl (meth)acrylates, especially chlorosulfonated polyethylenes or fluorine-containing polymers, sulfonamide-modified melamines or purified Montan waxes;

inorganic or organic fillers, especially ground or precipitated calcium carbonates, with or without a coating of fatty acids, more particularly of stearates, barytes (heavy spar), talcs, finely ground quartzes, silica sand, iron mica, dolomites, wollastonites, kaolins, mica (potassium aluminum silicate), molecular sieves, aluminum oxides, aluminum hydroxides, magnesium hydroxide, silicas, cements, gypsums, flyashes, carbon black, graphite, metal powders such as aluminum, copper, iron, zinc, silver or steel, PVC powders or hollow beads;

fibers, especially glass fibers, carbon fibers, metal fibers, ceramic fibers, or polymeric fibers such as polyamide fibers or polyethylene fibers;

pigments, especially titanium dioxide and/or iron oxides;

the aforementioned accelerators;

rheology modifiers, especially thickeners or antisettling agents;

adhesion promoters, especially organoalkoxysilanes;

stabilizers against oxidation, heat, light or UV radiation;

flame retardants, especially aluminum hydroxide (ATH), magnesium dihydroxide (MDH), antimony trioxide, antimony pentoxide, boric acid (B(OH)$_3$), zinc borate, zinc phosphate, melamine borate, melamine cyanurate, ammonium polyphosphate, melamine phosphate, melamine pyrophosphate, polybrominated diphenyl oxides or diphenyl ethers, phosphates such as especially diphenyl cresyl phosphate, resorcinol bis(diphenyl phosphate), resorcinol diphosphate oligomer, tetraphenylresorcinol diphosphite, ethylenediamine diphosphate or bisphenol A bis(diphenyl phosphate), tris(chloroethyl) phosphate, tris(chloropropyl) phosphate or tris(dichloroisopropyl) phosphate, tris[3-bromo-2,2-bis-(bromomethyl)propyl] phosphate, tetrabromobisphenol A, bis(2,3-dibromopropyl ether) of bisphenol A, brominated epoxy resins, ethylenebis(tetrabromophthalimide), ethylenebis(dibromonorbornanedicarboximide), 1,2-bis(tribromophenoxy)ethane, tris(2,3-dibromopropyl) isocyanurate, tribromophenol, hexabromocyclododecane, bis(hexachlorocyclopentadieno)cyclooctane or chlorinated paraffins;

surface-active substances, especially wetting agents, flow control agents, deaerating agents or defoamers;

biocides, such as, for example, algicides, fungicides or fungal growth inhibitors.

The epoxy resin composition preferably comprises further auxiliaries and adjuvants, especially wetting agents, flow control agents, defoamers, stabilizers, pigments and/or accelerators, especially salicylic acid and/or 2,4,6-tris(dimethylam inomethyl)phenol.

The epoxy resin composition preferably contains none or only a small amount of unincorporable diluents, preferably not more than 5 weight %, especially not more than 2 weight %.

The ratio of the number of groups that are reactive toward epoxide groups in the epoxy resin composition, to the number of epoxide groups, is preferably in the range from 0.5 to 1.5, more particularly 0.7 to 1.2.

The amine hydrogens and, where present, other groups that are reactive toward epoxide groups, present in the epoxy resin composition, react with the epoxide groups with ring-opening of the latter groups (addition reaction). As a result of these reactions, the composition undergoes polymerization and ultimately cures. The person skilled in the art is aware that primary amino groups are difunctional groups with respect to epoxide groups, and a primary amino group therefore counts as two groups that are reactive toward epoxide groups.

The two components of the epoxy resin composition are each stored in their own container. Further constituents of the epoxy resin composition may be present as part of the resin component or of the hardener component, with further constituents that are reactive toward epoxide groups preferably being part of the hardener component. A suitable container for storing the resin component or the hardener component is, in particular, a drum, a hobbock, a pouch, a pail, a canister, a cartridge or a tube. The components are storable, meaning that they can be kept for several months up to a year or more before being employed, without suffering alteration in their respective properties to any extent relevant for their use. For the use of the epoxy resin composition, the resin component and the hardener component are mixed with one another shortly before or during application. The mixing ratio between the two components is preferably selected such that the groups of the hardener component that are reactive toward epoxide groups are present in an appropriate ratio to the epoxide groups of the resin component, as described above. In terms of parts by weight, the mixing ratio between the resin component and the hardener component is customarily in the range from 1:10 to 10:1.

The two components are mixed by means of suitable method; this may take place continuously or batchwise. If mixing takes place prior to application, it should be ensured that not too much time elapses between the mixing of the components and application, since otherwise there may be disruptions, such as retarded or incomplete development of adhesion to the substrate, for example. Mixing takes place in particular at ambient temperature, which is typically in the range from about 5 to 50° C., preferably at about 10 to 30° C. The mixing of the two components is at the same time the start of curing through chemical reaction, as described above. Curing typically takes place at a temperature in the range from 0 to 150° C. It preferably takes place at ambient temperature and typically extends over several days to weeks. The duration is dependent on factors including the temperature, the reactivity of the constituents and their stoichiometry, and also the presence of accelerators.

The epoxy resin composition is applied to at least one substrate, those below being particularly suitable:

glass, glass-ceramic, concrete, mortar, brick, tile, plaster or natural stones such as granite or marble;

metals or alloys such as aluminum, iron, steel or nonferrous metals, or surface-enhanced metals or alloys such as galvanized or chromed metals;

leather, textiles, paper, wood, woodbase materials bonded with resins, such as phenolic, melamine or epoxy resins, for example, resin-textile composites, or other polymer composites;

plastics, especially rigid or flexible PVC, ABS, polycarbonate (PC), polyamide (PA), polyesters, PMMA, epoxy resins, PU, POM, PO, PE, PP, EPM or EPDM, the plastics having optionally been surface-treated by plasma, corona or flame treatment;

fiber-reinforced plastics, such as carbon fiber-reinforced plastics (CRP), glass fiber-reinforced plastics (GRP) or sheet molding compounds (SMC);

coated substrates, such as powder-coated metals or alloys;

paints or varnishes.

As and when necessary, the substrates may be pretreated before the epoxy resin composition is applied. Such pretreatments include, in particular, physical and/or chemical cleaning techniques, as for example sanding, sandblasting, shotblasting, brushing and/or blowing, and also, furthermore, treatment with cleaners or solvents, or the application of an adhesion promoter, an adhesion promoter solution or a primer.

The epoxy resin composition described can be used with advantage as a fiber composite matrix for fiber composite materials (composites), as an encapsulating compound, sealant, adhesive, covering, coating, paint, varnish, seal, priming coat or primer, and for cement products such as cement-based repair mortars or grout.

With preference it can be used as a fiber composite matrix for fiber composite materials (composites) such as, in particular, CRP or GRP;

an adhesive, more particularly as a bodywork adhesive, sandwich element adhesive, half-shell adhesive for rotor blades of wind turbines, bridge element adhesive or anchoring adhesive; or as a coating, covering or paint, more particularly as a varnish, seal, priming coat or primer for construction or industry applications, or as a floor covering or floor coating for interiors such as offices, industrial halls, sports halls or cooling rooms, or as a floor covering or floor coating in the exterior segment, for balconies, terraces, parking decks, bridges or roofs, or as a protective coating for concrete, cement, metals, plastics or wood, for the surface sealing of wooden constructions, vehicles, loading areas, tanks, silos, shafts, piping circuits, pipelines, machines or steel constructions, for example, such as of boats, piers, offshore platforms, sluice gates, hydroelectric power stations, river constructions, swimming pools, wind turbines, bridges, chimneys, cranes or sheet-pile walls, for example, in particular also for heavy-duty corrosion protection; or as an undercoat, tie coat, anticorrosion primer, or for rendering surfaces hydrophobic.

In particular, the epoxy resin composition described can be used in low-emission products that carry eco-quality seals, according for example to Emicode (EC1 Plus), AgBB, DIBt, Der Blaue Engel, AFSSET, RTS (M1), and US Green Building Council (LEED).

The fully or partly cured epoxy resin composition, especially when used as a coating, covering or paint, may have a further coating, covering or paint applied to it, in which case this further layer may likewise comprise an epoxy resin composition, or else may comprise a different material, particularly a polyurethane coating or polyurea coating.

As a coating, the epoxy resin composition is used advantageously in a method for coating, where it has a liquid consistency with low viscosity and good leveling properties and is applied more particularly as a self-leveling or thixotrope coating to predominantly planar surfaces or as a paint. In the context of this application, the viscosity of the epoxy resin composition immediately after the mixing of the resin and hardener components, and as measured at 20° C., is preferably in the range from 300 to 4000 mPa·s, preferably in the range from 300 to 3000 mPa·s. Within the working time, the mixed composition is applied two-dimensionally as a thin film having a layer thickness of typically about 50 μm to about 5 mm to a substrate, typically at ambient temperature. Application is accomplished in particular by pouring the composition onto the substrate that is to be coated, and then spreading it evenly with the aid, for example, of a doctor blade or toothed applicator. Application may, however, alternatively take place with a brush or roller or by spray application, as an anticorrosion coating on steel, for example.

Curing is typically accompanied by the development of largely clear, glossy and nonsticky films of high-hardness, which exhibit effective adhesion to a very wide variety of substrates.

The use of the epoxy resin composition results in an article comprising the cured composition from the curing of the epoxy resin composition described.

EXAMPLES

Set out below are working examples which are intended to elucidate in more detail the invention described. The invention is of course not confined to these working examples described.

"AHEW" stands for the amine hydrogen equivalent weight.

"EEW" stands for the epoxide equivalent weight.

"Standard conditions" refer to a temperature of 23±1° C. and a relative atmospheric humidity of 50±5%. "SC" stands for "standard conditions".

Description of Measurement Methods:

Infrared spectra (FT-IR) were measured as undiluted films on an FT-IR instrument 1600 from Perkin-Elmer equipped with a horizontal ATR measurement unit with ZnSe crystal; the absorption bands are reported in wavenumbers ($cm^{-1}$); (measuring window: 4000-650 $cm^{-1}$).

The viscosity was measured on a thermostated cone/plate viscometer, Rheotec RC30 (cone diameter 50 mm, cone angle 1°, cone tip/plate distance 0.05 mm, shear rate 10 $s^{-1}$).

The amine number was determined by titration (with 0.1N $HClO_4$ in acetic acid against crystal violet).

Substances Used:

Araldite® GY 250: bisphenol A diglycidyl ether, EEW about 187.5 g/eq (from Huntsman)

Araldite® DY-E: monoglycidyl ether of $C_{12}$ to $C_{14}$ alcohols, EEW about 290 g/eq (from Huntsman)

Ancamine® K 54: 2,4,6-tris(dimethylaminomethyl)phenol (from Air Products)

EP adduct 1: reaction product of 116.0 g 1,5-diamino-2-methylpentane with 200.2 g of Araldite® DY-K;
AHEW about 109.5 g/eq; viscosity (20° C.) about 13.1 Pa·s Araldite® DY-K: cresyl glycidyl ether, EEW about 182 g/eq (from Huntsman)

Jeffamine® D-230: polyoxypropylenediamine with average molecular weight of about 240 g/mol, AHEW about 60 g/eq (from Huntsman)

Gaskamine® 240: styrenized 1,3-bis(aminomethyl)benzene; AHEW 103 g/eq; viscosity (20° C.) 165 mPa·s (from Mitsubishi Gas Chemical)

N-Benzyl-1,2-propanediamine: reaction mixture prepared as described below

N-Benzyl-1,2-propanediamine:

A round-bottomed flask was charged at room temperature with 444.8 g (6 mol) of 1,2-propanediamine under a nitrogen atmosphere. With thorough stirring, a solution of 212.2 g (2 mol) of benzaldehyde in 1500 ml of isopropanol was added slowly dropwise with stirring continued for 2 hours thereafter. The reaction mixture was subsequently hydrogenated under a hydrogen pressure of 90 bar at a temperature of 85° C. and with a flow rate of 5 ml/min on a continuous hydrogenation apparatus with Pd/C fixed-bed catalyst. For reaction monitoring, IR spectroscopy was used to verify whether the imine band at about 1665 $cm^{-1}$ had disappeared. At that point the hydrogenated solution was concentrated at 65° C. on a rotary evaporator, with removal of unreacted 1,2-propanediamine and isopropanol. This gave a clear, slightly yellowish liquid. Of this, 300 g were distilled under reduced pressure at 80° C., and 237.5 g of distillate with a vapor temperature of 60 to 63° C. at 0.08 to 0.09 bar were collected. This gave a colorless liquid having a viscosity of 8.5 mPa·s at 20° C. and an amine number of 682 mg KOH/g, which, according to $^1$H-NMR, gave a mixture of $N^1$-benzyl-1,2-propanediamine and $N^2$-benzyl-1,2-propanediamine in a ratio of about 2/1.

Preparation of Amines of Formula (I)

Amine 1: reaction mixture comprising 1,4-bis(aminopropylaminomethyl)benzene

A round-bottomed flask was charged at room temperature with 74.1 g (1.0 mol) of 1,2-propanediamine under a nitrogen atmosphere. With thorough stirring, a solution of 26.8 g (0.2 mol) of terephthalic aldehyde in 500 ml of dioxane was added slowly dropwise, followed by stirring for 30 minutes more. The reaction mixture was hydrogenated under a hydrogen pressure of 85 bar, at a temperature of 85° C. and with a flow rate of 5 ml/min, on a continuous hydrogenation apparatus with Pd/C fixed-bed catalyst. To monitor the reaction, IR spectroscopy was used to verify whether the imine band at about 1665 $cm^{-1}$ had disappeared. At that point the excess 1,2-propylenediamine and the solvent were removed on a rotary evaporator at 65° C. and 1 mbar. This gave a clear, yellowish liquid having a viscosity of 4.13 Pa·s at 20° C. and an amine number of 768.8 mg KOH/g.

FT-IR: 2959, 2913, 2890, 2852, 1454, 1366, 1288, 1254, 1117, 1082, 1048, 890, 870.

Amine 2: reaction mixture comprising 1,4-bis(aminopropylaminomethyl)benzene

A round-bottomed flask was charged at room temperature with 111.2 g (1.5 mol) of 1,2-propanediamine under a nitrogen atmosphere. With thorough stirring, a solution of 26.8 g (0.2 mol) of terephthalic aldehyde in 600 ml of dioxane, heated to 50° C., was added slowly dropwise, followed by stirring for 30 minutes more. The reaction mixture was hydrogenated under a hydrogen pressure of 90 bar, at a temperature of 90° C. and with a flow rate of 5 ml/min, on a continuous hydrogenation apparatus with Pd/C fixed-bed catalyst. To monitor the reaction, IR spectroscopy was used to verify whether the imine band at about 1665 $cm^{-1}$ had disappeared. At that point the excess 1,2-propylenediamine and the solvent were removed on a rotary evaporator at 65° C. and 1 mbar. This gave a clear, pale yellow liquid having a viscosity of 0.24 Pa·s at 20° C. and an amine number of 849.2 mg KOH/g.

FT-IR: 2959, 2800, 1567, 1500, 1440, 1367, 1100, 1010, 1048, 810.

Production of Hardeners and Epoxy Resin Compositions

For each example, the ingredients specified in table 1 or 2 were mixed in the stated quantities (in parts by weight) of the hardener component using a centrifugal mixer (Speed-Mixer™ DAC 150, FlackTek Inc.) and the mixtures were stored in the absence of moisture.

Similarly, the ingredients of the resin component as specified in table 1 or 2 were processed and stored.

Thereafter the two components of each composition were processed to a homogeneous liquid using the centrifugal mixer, and this liquid was tested immediately as follows:

10 minutes after mixing, the viscosity at 20° C. was ascertained ("viscosity (10')").

A first film was drawn down in a film thickness of 500 μm onto a glass plate, which was stored/cured under standard conditions. Determined on this film was the König hardness (pendulum hardness as König, measured to DIN EN ISO 1522) after 1 day ("König hardness (1 d SC)"), after 2 days ("König hardness (2 d SC)"), after 4 days ("König hardness (4 d SC)"), after 7 days ("König hardness (7 d SC)"), and after 14 days ("König hardness (14 d SC)"). After 14 days, the appearance of the film was assessed (identified in the table as "appearance (SC)". A film identified as "attractive" there was clear and had a glossy and nonsticky surface without structure. "Structure" here refers to any kind of marking or pattern on the surface.

A second film was drawn down onto a glass plate in a film thickness of 500 μm, and this film immediately after application was stored, or cured, at 8° C. and at 80% relative humidity for 7 days and subsequently under standard conditions (SC) for 3 weeks. 24 hours after application, a polypropylene bottle cap was placed onto the film, with a moist sponge placed beneath the cap. After a further 24 hours, the sponge and the cap were removed and were placed on a new site on the film, where, after 24 hours, they were removed again and placed anew, a total of 4 times. Thereafter the appearance of this film was assessed (identified in the tables as "appearance (8°/80%)"), in the same way as described for the appearance (SC). Also reported here in each case is the number of marks visible in the film as a result of the wet sponge and/or the applied cap. On the films cured in this way, the König hardness was again determined, in each case after 7 days at 8° C. and 80% relative humidity ("König hardness (7 d 8°/80%)"), then after a further 2 days under standard conditions ("König hardness (+2 d SC)"), 7 days under standard conditions ("König hardness (+7 d SC)"), and after 2 weeks under standard conditions ("König hardness (+14 d SC)").

The results are reported in table 1 or 2.

The epoxy resin compositions EZ-1 to EZ-8 are inventive examples. The epoxy resin compositions Ref-1 and Ref-2 are comparative examples.

TABLE 1

Composition and properties of EZ-1 to EZ-4 and Ref-1 to Ref-2.

| Example | | EZ-1 | EZ-2 | EZ-3 | EZ-4 | Ref-1 | Ref-2 |
|---|---|---|---|---|---|---|---|
| Resin comp.: | | | | | | | |
| Araldite ® GY-250 | | 167.2 | 167.2 | 167.2 | 167.2 | 167.2 | 167.2 |
| Araldite ® DY-E | | 31.8 | 31.8 | 31.8 | 31.8 | 31.8 | 31.8 |
| Hardener comp.: | | | | | | | |
| Amine 1 | | 39.4 | 41.7 | 54.3 | — | — | — |
| Amine 2 | | — | — | — | 41.7 | — | — |
| EP adduct 1 | | — | — | — | — | 109.5 | 109.5 |
| Ancamine ® K 54 | | 4.8 | — | — | — | 6.2 | — |
| Viscosity (10') [Pa · s] | | 2.4 | 2.3 | 2.6 | 1.6 | 4.6 | 4.6 |
| König | (1 d SC) | 91 | 39 | 109 | 109 | 108 | 63 |
| hardness [s] | (2 d SC) | 134 | 71 | 140 | 140 | 147 | 85 |
| | (4 d SC) | 167 | 94 | 155 | 144 | 168 | 105 |
| | (7 d SC) | 188 | 104 | 157 | 161 | 176 | 121 |
| | (14 d SC) | 203 | 111 | 161 | n.d. | 185 | 140 |
| Appearance (SC) | | attractive | attractive | attractive | attractive | attractive | attractive |
| König | (7 d 8°/80%) | 42 | 21 | 46 | 11 | 53 | 37 |
| hardness [s] | (+2 d SC) | 59 | 28 | 64 | 15 | 129 | 94 |
| | (+7 d SC) | 76 | 34 | 77 | n.d. | 161 | 113 |
| | (+14 d SC) | 125 | 34 | 80 | n.d. | 183 | 125 |
| Appearance (8°/80%) | | slightly matt | slightly matt | slightly matt | attractive | slightly matt | slightly matt |
| Number of marks | | 1 | 1 | 1 | none | 2 | 2 |

"n.d." stands for "not determined"

TABLE 2

Composition and properties of EZ-5 to EZ-8.

| Example | | EZ-5 | EZ-6 | EZ-7 | EZ-8 |
|---|---|---|---|---|---|
| Resin comp.: | | | | | |
| Araldite ® GY-250 | | 167.2 | 167.2 | 167.2 | 167.2 |
| Araldite ® DY-E | | 31.8 | 31.8 | 31.8 | 31.8 |
| Hardener comp.: | | | | | |
| Amine 1 | | 29.2 | 20.9 | 20.9 | — |
| Amine 2 | | — | — | — | 25.0 |
| Jeffamine ® D-230 | | 18.0 | — | — | — |
| Gaskamine ® 240 | | — | 51.5 | — | — |
| N-Benzyl-1,2-propanediamine | | — | — | 27.4 | 27.4 |
| Viscosity (10') [Pa · s] | | 1.11 | 0.93 | 0.71 | 0.58 |
| König hardness [s] | (1 d SC) | 15 | 55 | 50 | 109 |
| | (2 d SC) | 80 | 123 | 136 | 155 |
| | (4 d SC) | 97 | 144 | 153 | 176 |
| | (7 d SC) | 106 | 157 | 158 | 185 |
| | (14 d SC) | 132 | 178 | 170 | n.d. |
| Appearance (NK) | | attractive | attractive | attractive | attractive |
| König hardness [s] | (7 d 8°/80%) | 3 | 24 | 25 | 38 |
| | (+2 d SC) | 4 | 50 | 40 | 50 |
| | (+7 d SC) | 6 | 66 | 55 | n.d. |
| | (+14 d SC) | 8 | 85 | 55 | n.d. |
| Appearance (8°/80%) | | tacky | slightly matt | slightly matt | attractive |
| Number of marks | | 1 | 1 | 1 | none |

"n.d." stands for "not determined"

The invention claimed is:

1. An amine of formula (I)

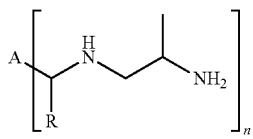

wherein
n is 2 or 3,
R is a hydrogen radical or is methyl or phenyl, and
A is a radical selected from the group consisting of:

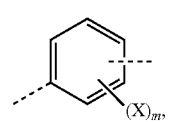 formula (IIa)

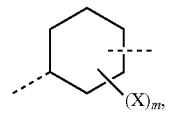 formula (IIb)

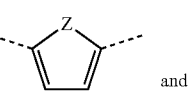 formula (IIc)

and

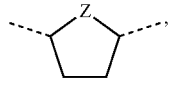 formula (IId)

wherein
m is 0, 1, or 2,
X is a radical independently selected from the group consisting of alkyl and alkoxy having 1 to 4 carbon atoms, and
Z is an oxygen atom or a sulfur atom.

2. The amine of the formula (I) as claimed in claim 1, wherein n is 2.

3. The amine of the formula (I) as claimed in claim 1, wherein R is a hydrogen radical.

4. A process for preparing an amine of the formula (I) as claimed in claim 1 comprising subjecting 1,2-propylenediamine to reductive alkylation with at least one di- or trifunctional carbonyl compound of the formula (III) and hydrogen

5. The process as claimed in claim 4, wherein 1,2-propylenediamine is used in stoichiometric excess over the carbonyl groups of the carbonyl compound of the formula (III).

6. A method comprising hardening epoxy resins with an amine of the formula (I) as claimed in claim 1.

7. A hardener for epoxy resins comprising:
at least one amine of the formula (I) as claimed in claim 1, and
at least one further amine and/or at least one accelerator.

8. The hardener as claimed in claim 7, wherein the accelerator is salicylic acid or 2,4,6-tris(dimethylaminomethyl)phenol or a combination thereof.

9. The hardener as claimed in claim 7, wherein the further amine comprises 1-(2-aminopropylaminomethyl)-4-(1-aminoprop-2-ylaminomethyl)benzene or 1,4-bis(1-aminoprop-2-ylaminomethyl)benzene or 1-(2-aminopropylaminomethyl)-4-(1-aminoprop-2-ylaminomethyl)cyclohexane or 1,4-bis(1-aminoprop-2-ylaminomethyl)cyclohexane.

10. The hardener as claimed in claim 7, wherein the further amine comprises a partially styrenized polyamine or a product of the reductive alkylation of primary aliphatic polyamines with monofunctional aldehydes or ketones.

11. The hardener as claimed in claim 7, wherein the hardener contains not more than 10 weight % of unincorporable diluents.

12. An epoxy resin composition comprising:
a resin component comprising at least one epoxy resin, and
a hardener component comprising at least one amine of the formula (I) as claimed in claim 1.

13. A method comprising applying an epoxy resin composition as claimed in claim 12 as a fiber composite matrix for fiber composite materials, an adhesive, a coating, a covering, or a finish.

14. An amine that
is 1,4-bis(2-aminopropylaminomethyl)benzene or 1,4-bis(2-aminopropylaminomethyl)cyclohexane.

15. A method comprising hardening epoxy resins with an amine as claimed in claim 14.

16. A hardener for epoxy resins comprising at least one amine as claimed in claim 14, and
at least one further amine and/or at least one accelerator.

17. An epoxy resin composition comprising:
a resin component comprising at least one epoxy resin, and
a hardener component comprising at least one amine as claimed in claim 14.

18. A method comprising applying an epoxy resin composition as claimed in claim 17 as a fiber composite matrix for fiber composite materials, an adhesive, a coating, a covering, or a finish.

* * * * *